US009320578B2

(12) United States Patent
Kuwamura

(10) Patent No.: US 9,320,578 B2
(45) Date of Patent: Apr. 26, 2016

(54) ARTICULATOR

(75) Inventor: Yasuhiko Kuwamura, Kameoka (JP)

(73) Assignee: NISSIN DENTAL PRODUCTS INC., Kyoto (JP)

( * ) Notice: Subject to any disclaimer, the term of this patent is extended or adjusted under 35 U.S.C. 154(b) by 48 days.

(21) Appl. No.: 13/372,338

(22) Filed: Feb. 13, 2012

(65) Prior Publication Data

US 2012/0207535 A1    Aug. 16, 2012

(30) Foreign Application Priority Data

Feb. 14, 2011 (JP) ................................. 2011-028371
Jan. 11, 2012 (JP) ................................. 2012-002750

(51) Int. Cl.
*A61C 11/00* (2006.01)
*A61C 11/02* (2006.01)

(52) U.S. Cl.
CPC ....... *A61C 11/022* (2013.01); *Y10T 403/32606* (2015.01)

(58) Field of Classification Search
CPC ...... A61C 11/02; A61C 11/022; A61C 11/08; A61C 11/003; A61C 11/084; A61C 11/00; A61C 11/082; A61C 11/001; A61C 11/087; Y10T 403/32606
USPC ...................... 433/57–67; 434/264; D24/128; 403/112, 113, 119, 150–159, 161–163
See application file for complete search history.

(56) References Cited

U.S. PATENT DOCUMENTS

| | | | | |
|---|---|---|---|---|
| 2,816,360 A | * | 12/1957 | Stuart | 433/55 |
| 2,884,696 A | * | 5/1959 | Bonfanti | 433/56 |
| 4,045,873 A | * | 9/1977 | Burnett | 433/58 |
| 4,047,302 A | * | 9/1977 | Cheythey | 433/56 |
| 4,439,150 A | * | 3/1984 | Edwardson | 433/56 |
| 4,453,918 A | * | 6/1984 | Edwardson | 433/55 |
| 5,267,858 A | * | 12/1993 | Ono | 433/58 |
| 5,645,425 A | * | 7/1997 | Callne | 433/54 |
| 2006/0204921 A1 | * | 9/2006 | Uhm | 433/60 |
| 2006/0261605 A1 | * | 11/2006 | Ku et al. | 292/251.5 |
| 2009/0123898 A1 | * | 5/2009 | Lee et al. | 434/264 |

FOREIGN PATENT DOCUMENTS

| | | |
|---|---|---|
| CN | 1679452 A | 10/2005 |
| CN | 201350136 Y | 11/2009 |

(Continued)

OTHER PUBLICATIONS

European Search Report for European Application No. 12155104.8, mailed May 8, 2012.

(Continued)

*Primary Examiner* — Matthew Nelson
(74) *Attorney, Agent, or Firm* — Pearl Cohen Zedek Latzer Baratz LLP

(57) ABSTRACT

An articulator can more simply configure a coupling mechanism between a lower jaw support portion and an upper jaw support portion at a joint portion. An articulator includes a first support portion; a second support portion; and a joint portion that couples the first support portion and the second support portion. The joint portion includes: a pair of projecting portions; and an engaging support portion. The projecting portion and the engaging support portion are attractable to each other by way of magnetic force.

19 Claims, 13 Drawing Sheets

(56) References Cited

FOREIGN PATENT DOCUMENTS

| | | | |
|---|---|---|---|
| JP | 1995-095990 A | 4/1995 |
| JP | 2009-125086 | 6/2009 |
| WO | WO 01/95827 A1 | 12/2001 |
| WO | WO 2008/089528 A2 | 7/2008 |

OTHER PUBLICATIONS

Office Action for CN Application No. 201210029557.9, mailed Feb. 27, 2014.

Office Action for Japan Patent Application No. 2012-002750, dated Nov. 17, 2015.

* cited by examiner

ARTICULATOR

This application is based on and claims the benefit of priority from Japanese Patent Application No. 2011-028371, filed on Feb. 14, 2011, and Japanese Patent Application No. 2012-002750, filed on Jan. 11, 2012, the contents of both of which is incorporated herein by reference.

BACKGROUND OF THE INVENTION

1. Field of the Invention

The present invention relates to an articulator.

2. Related Art

In the field of dentistry, an articulator has conventionally been used that replicates jaw movements of the human body such as when fabricating an artificial tooth or dental prosthesis. Such an articulator is provided with an upper jaw support portion to which an upper jaw model is fixed, a lower jaw support portion to which a lower jaw model is fixed, and a joint portion that rotatably couples this upper jaw support portion and lower jaw support portion.

Furthermore, in order to enable more precise replication of the jaw movements of the human body, another articulator has also been proposed in which a joint portion is configured to include a projecting portion provided at an upper jaw support portion, a U-shaped groove portion provided at the lower jaw support portion and engaged with the projecting portion, and an elastic body coupled to the projecting portion to pull the projecting portion to the bottom side of the groove portion (for example, refer to Japanese Unexamined Patent Application, Publication No. 2009-125086).

According to the articulator disclosed in Japanese Unexamined Patent Application, Publication No. 2009-125086, the lower jaw support portion and the upper jaw support portion are rotatably coupled with each other with the projecting portion as a fulcrum. Furthermore, the upper jaw support portion is slidably coupled to the lower jaw support portion by the projecting portion being guided in the groove portion. Moreover, the projecting portion is pulled toward the bottom side of the groove portion by way of an elastic body such as a rubber band or a spring to be retained at a predetermined position. In this way, the articulator disclosed in Japanese Unexamined Patent Application, Publication No. 2009-125086 is configured such that the upper jaw support portion and the lower jaw support portion can be moved vertically and laterally, while the engaged position of the lower jaw support portion and the upper jaw support portion, i.e. an engaged position of the projecting portion with the groove portion is retained at a predetermined position (for example, a centric position).

SUMMARY OF THE INVENTION

However, since the articulator disclosed in Japanese Unexamined Patent Application, Publication No. 2009-125086 is coupled so that the lower jaw support portion and the upper jaw support portion are engaged at a predetermined position by way of an elastic body, there has been a problem in that the coupling mechanism of the joint portion is complicated.

Therefore, it is an object of the present invention to provide an articulator that can more simply configure a coupling mechanism of a joint portion between a lower jaw support portion and an upper jaw support portion.

The present invention relates to an articulator comprising: a first support portion to which a first dental model is fixed at a front side of the first support portion and that supports the first dental model; a second support portion to which a second dental model is fixed at a front side of the second support portion and that supports the second dental model; and a joint portion that couples a rear side of the first support unit and a rear side of the second support unit, wherein the joint portion includes: a pair of projecting portions that is provided at the rear side of the first support portion and projects in left and right directions, respectively; and an engaging support portion that is provided at the rear side of the second support portion to engage with the pair of projecting portions so as to rotatably support the second support unit about the pair of projecting portions, and wherein the projecting portion and the engaging support portion are configured so as to be attractable to each other by way of magnetic force.

Furthermore, it is preferable that either one among the projecting portion and the engaging support portion is configured to include a magnet and the other one among the projecting portion and the engaging support portion is configured to include a magnetic material.

Furthermore, it is preferable that the engaging support portion includes a first retaining portion that is arranged at a base end side of the engaging support portion and retains the projecting portion by way of magnetic force, and a first guide portion that is formed continuously to the first retaining portion and extends in a first direction, and the second support portion is coupled to the first support portion to be slidable in the first direction with respect to the first support portion.

Furthermore, it is preferable that an attractive force between the projecting portion and the first retaining portion in a closed state in which the first support portion and the second support portion are closed is greater than an attractive force between the projecting portion and the first retaining portion in an opened state in which the first support portion and the second support portion are opened.

Furthermore, it is preferable that the articulator further includes: a retaining portion side magnet that is arranged at the first retaining portion; an attraction member that is arranged at a position on the projecting portion facing the first retaining portion and that can be attracted to the retaining portion side magnet in the closed state; and a projecting portion side magnet that is arranged at a position on the projecting portion facing the first retaining portion and that repels the retaining portion side magnet in the opened state.

Furthermore, it is preferable that the projecting portion includes a shaft portion that extends in a direction in which the projecting portion projects, and a spherical condyle portion provided at this shaft portion, wherein the engaging support portion engages with the condyle portion.

Furthermore, it is preferable that a tip end side of the first guide portion is opened and a width of the first guide portion at the tip end side thereof is configured to be smaller than a diameter of the condyle portion.

Furthermore, it is preferable that the engaging support portion includes: a second guide portion that is provided continuously to the first guide portion at the tip end side of the first guide portion and extends in a second direction; and a third guide portion that is provided continuously to the first guide portion and the second guide portion at the tip end side of the first guide portion and extends in a third direction.

According to the articulator of the present invention, it is possible to more simply configure a coupling mechanism of a joint portion between a lower jaw support portion and an upper jaw support portion.

DETAILED DESCRIPTION OF THE INVENTION

Figure 1:
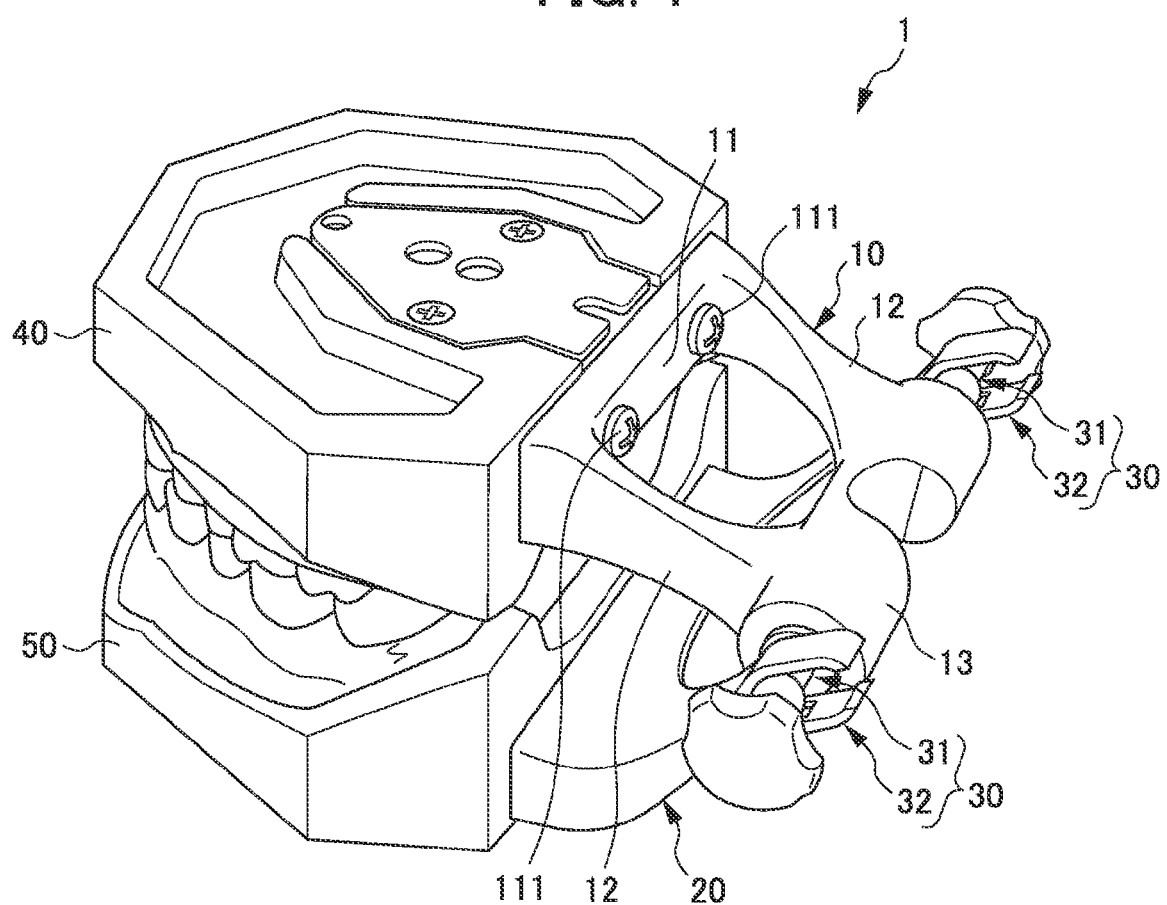
FIG. 1 is a perspective view showing an articulator according to a first embodiment of the present invention.

In the following, each of preferred embodiments for articulators of the present invention will be explained with reference to the drawings.

First, an articulator 1 according to a first embodiment will be explained with reference to FIGS. 1 to 10.

As shown in FIGS. 1 to 4, the articulator 1 according to the first embodiment is provided with an upper jaw support portion 10 that is a first support portion supporting an upper jaw model 40 as a first dental model, a lower jaw support portion 20 that is a second support portion supporting a lower jaw model 50 as a second dental model, and a joint portion 30 that couples these upper jaw support unit 10 and the lower jaw support unit 20.

It should be noted that, in the following explanation, the front-back, left-right, and vertical directions are defined with a side at which the front teeth of the upper jaw model 40 and the lower jaw model 50 fixed in the articulator 1 are arranged is established as the front.

The upper jaw support portion 10 is integrally formed from a rigid synthetic resin, and is provided with a plate-like upper jaw fixing portion 11 to which the upper jaw model 40 is fixed, a pair of upper jaw posteriorly extending portions 12 extending posteriorly from this upper jaw fixing portion 11, and a coupling portion 13 coupling each of the posterior ends of the pair of upper jaw posteriorly extending portions 12, as shown in FIGS. 1 to 6.

The upper jaw fixing portion 11 is configured to be in a horizontally long, rectangular, plate shape, and the upper jaw model 40 is fixed by screws 111 at a front face of this upper jaw fixing portion 11.

Figure 2:
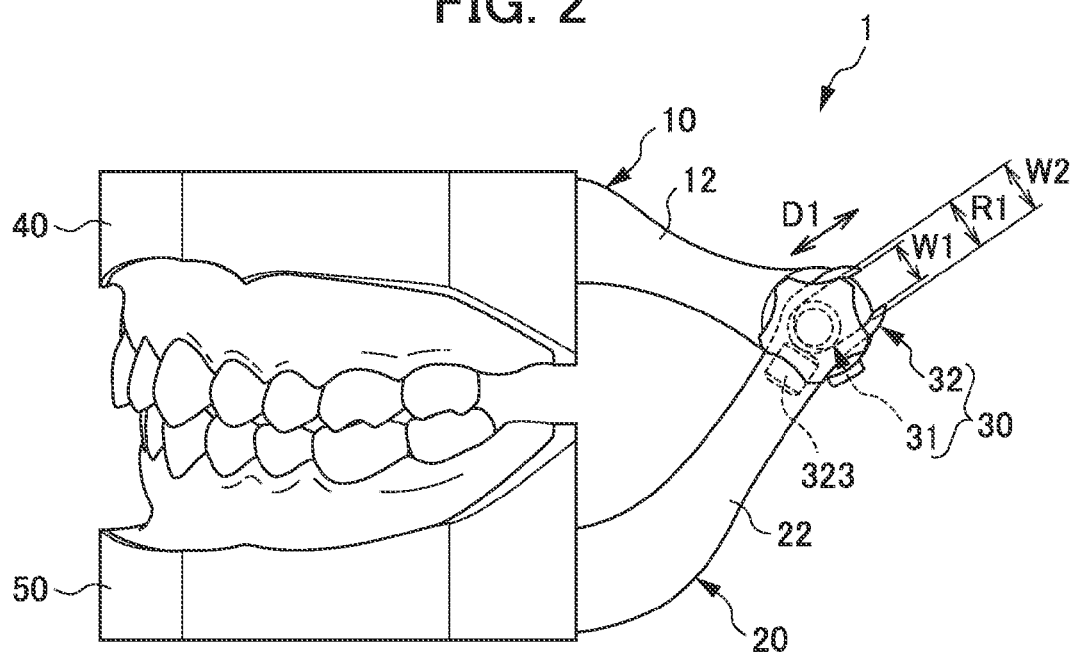
FIG. 2 is a lateral view of the articulator according to the first embodiment and shows a state in which an upper jaw support portion and a lower jaw support portion are closed.
Figure 5:
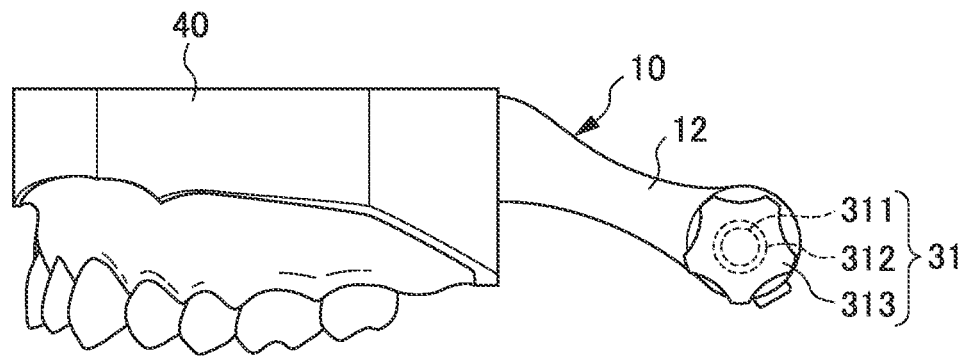
FIG. 5 is a lateral view of the upper jaw support portion of the articulator according to the first embodiment.

The pair of upper jaw posteriorly extending portions 12 extends posteriorly from one end and the other end in a longitudinal direction at a rear face of the upper jaw fixing portion 11. As shown in FIGS. 2 and 5, the pair of upper jaw posteriorly extending portions 12 extends obliquely downward in a state with the upper jaw model 40 fixed to the upper jaw fixing portion 11 being positioned horizontally.

The coupling portion 13 is formed in a cylindrical shape in which a center portion in a longitudinal direction is partially cut out. A screw hole (not illustrated) is formed in one end face and the other end face of this coupling portion 13 in a longitudinal direction, respectively.

The lower jaw support portion 20 is integrally formed from a rigid synthetic resin, and is provided with a plate-like lower jaw fixing portion 21 to which the lower jaw model 50 is fixed, and a pair of lower jaw posteriorly extending portions 22 extending posteriorly from this lower jaw fixing portion 21, as shown in FIGS. 1 to 4, 7 and 8.

The lower jaw fixing portion 21 is configured to be in a horizontally long, rectangular, plate shape, and the lower jaw model 50 is fixed by screws 211 at a front face of this lower jaw fixing portion 21.

Figure 7:
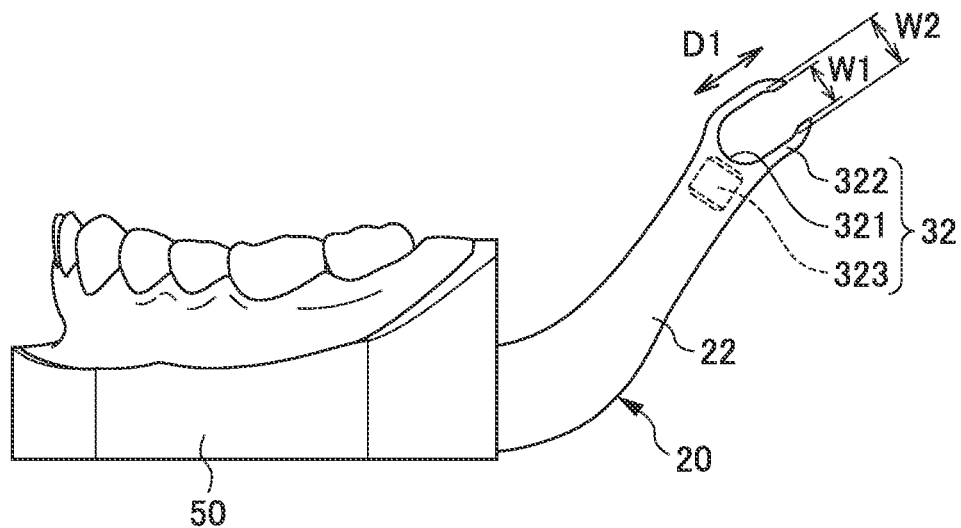
FIG. 7 is a lateral view of the lower jaw support portion of the articulator according to the first embodiment.
Figure 8:
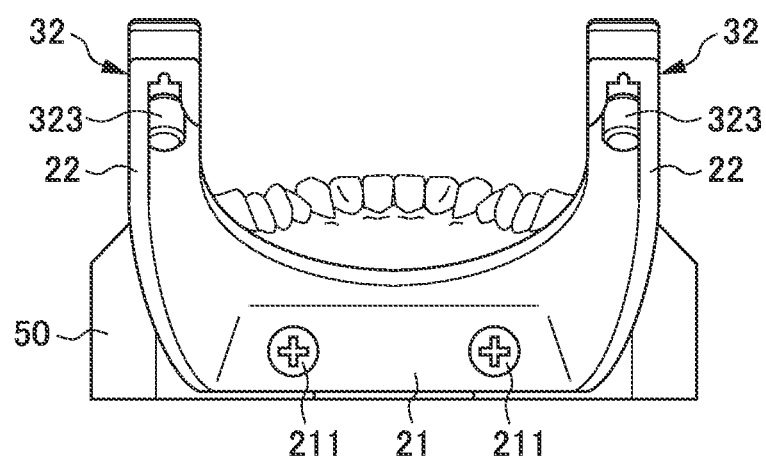
FIG. 8 is a rear view of the lower jaw support unit of the articulator according to the first embodiment.
Figure 9:
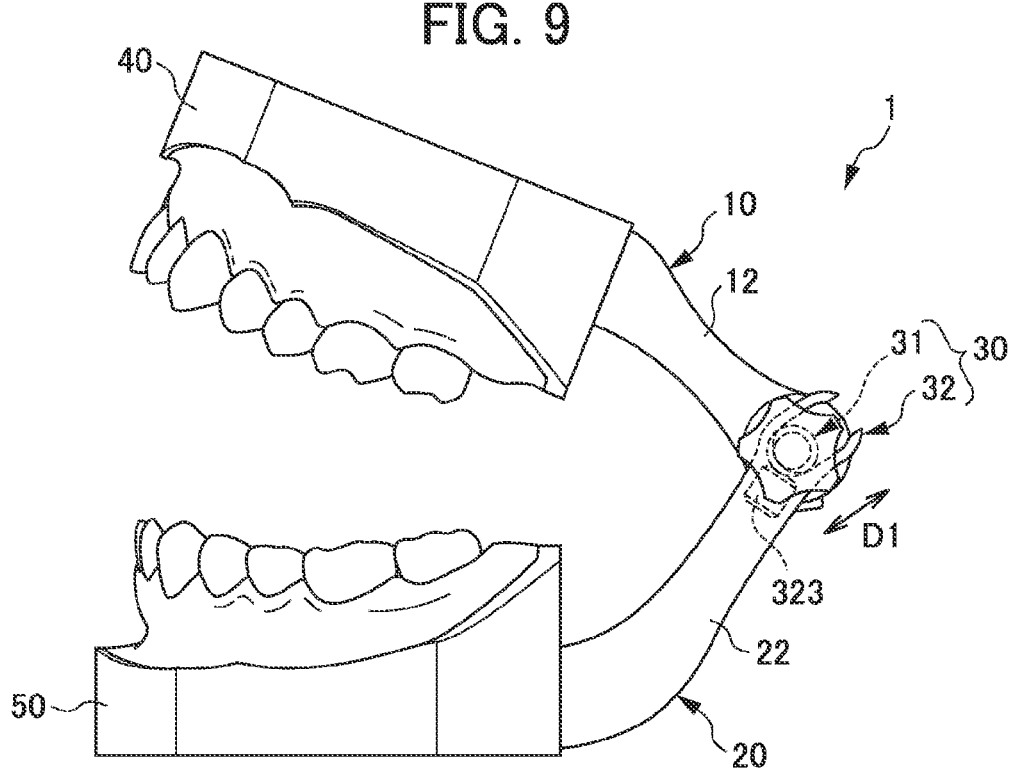
FIG. 9 is a lateral view of the articulator according to the first embodiment and shows a state in which the upper jaw support portion and the lower jaw support portion are opened.
Figure 10:
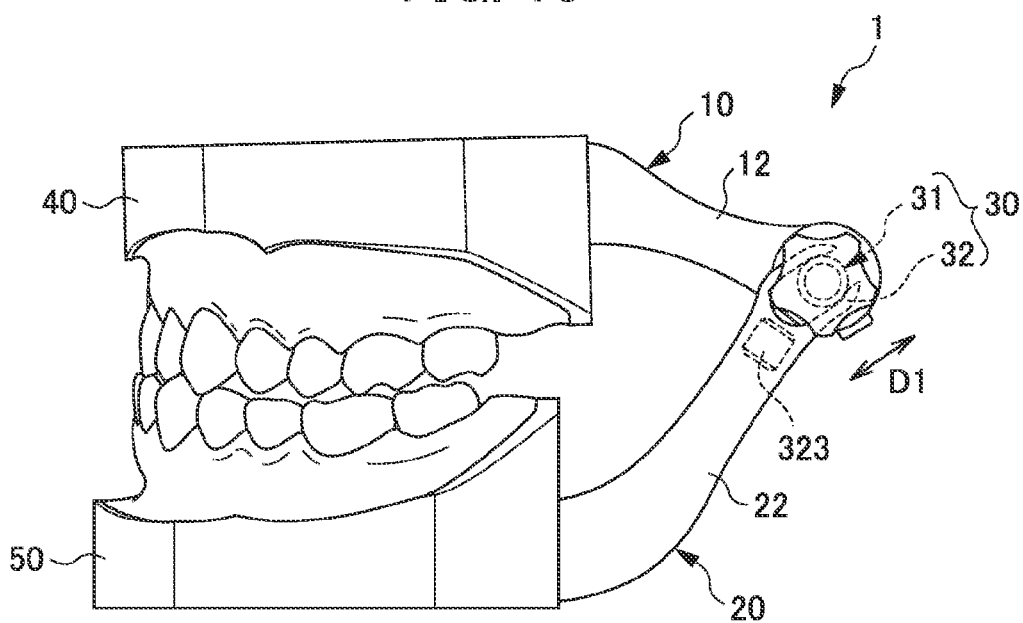
FIG. 10 is a lateral view of the articulator according to the first embodiment and shows the appearance when a projecting portion is made to slide from the state shown in FIG. 9.

The pair of lower jaw posteriorly extending portions 22 extends posteriorly from one end and the other end in a longitudinal direction at a rear face of the lower jaw fixing portion 21. As shown in FIGS. 2 and 7, the pair of lower jaw posteriorly extending portions 22 extends obliquely upward in a state with the lower jaw model 50 fixed to the lower jaw fixing portion 21 being positioned horizontally.

Figure 3:
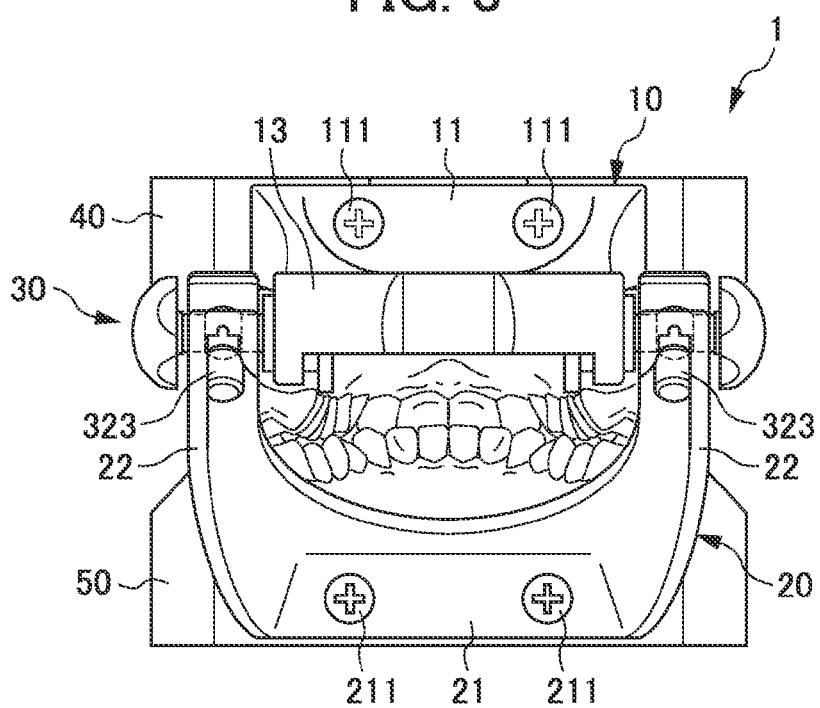
FIG. 3 is a rear view of the articulator according to the first embodiment.

As shown in FIGS. 1 to 3, the joint portion 30 is provided with a pair of projecting portions 31 provided at a rear side of the upper jaw support portion 10, and a pair of condyle path portions 32 as a pair of engaging support portions provided at a rear side of the lower jaw support portion 20.

Figure 4:
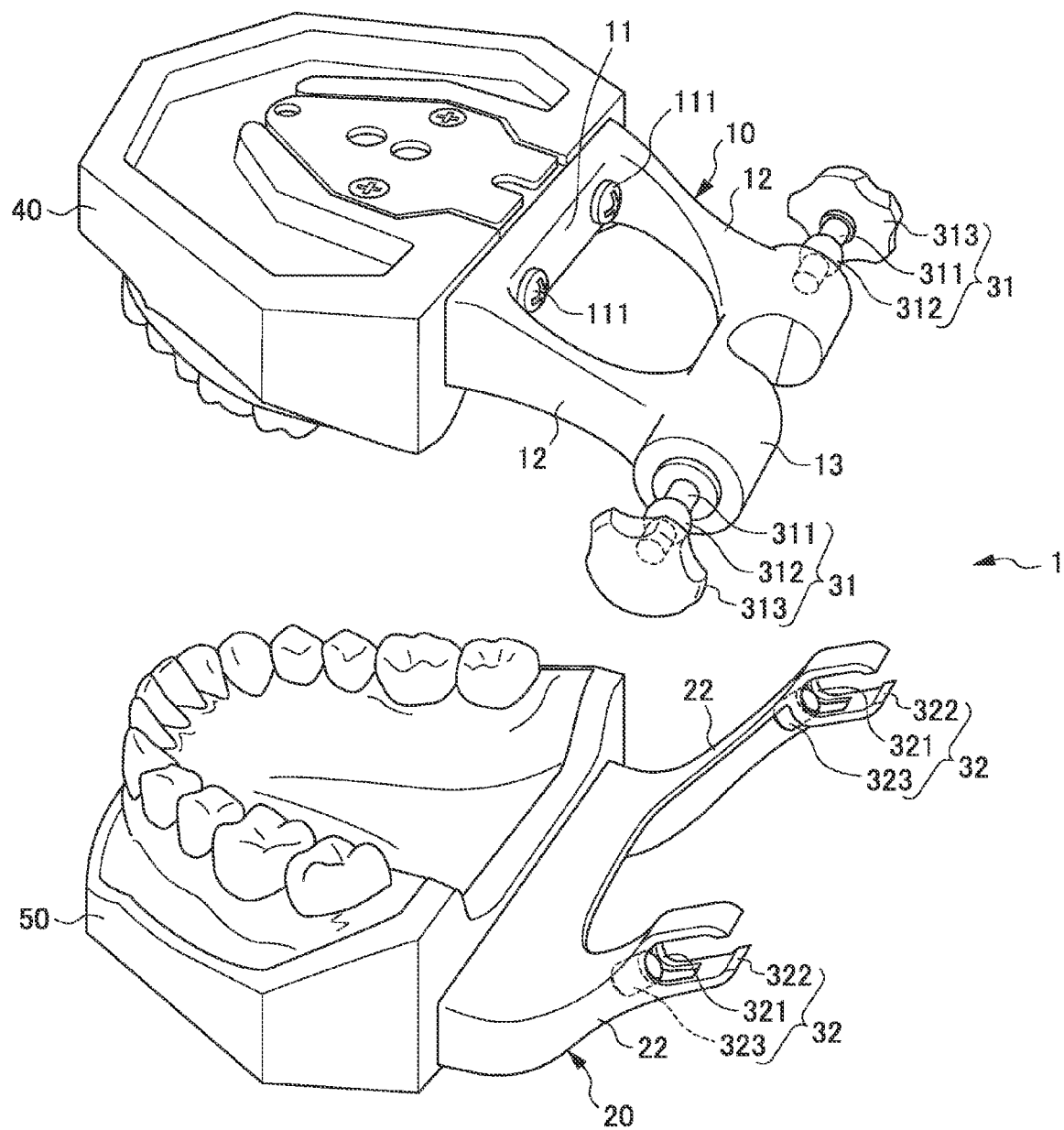
FIG. 4 is an exploded perspective view of the articulator according to the first embodiment.
Figure 6:
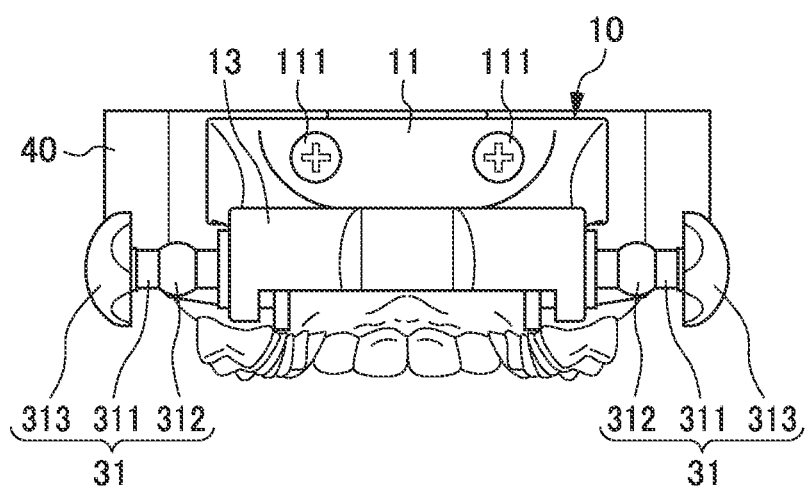
FIG. 6 is a rear view of the upper jaw support portion of the articulator according to the first embodiment.

As shown in FIGS. 4 and 6, the pair of projecting portions 31 projects externally from one end and the other end of the coupling portion 13. More specifically, one of the pair of projecting portions 31 projects to the left from a left side face of the upper jaw support unit 10 (coupling portion 13). Furthermore, the other one of the pair of projecting portions 31 projects to the right from a right side face of the upper jaw support unit 10 (coupling portion 13).

As shown in FIGS. 5 and 6, the projecting portion 31 is provided with shaft portions 311, condyle portions 312, and knob portions 313.

The shaft portions 311 extend substantially horizontally in right or left direction, and a pair of the shaft portions 311 is arranged coaxially. A screw thread (not shown) is formed at a peripheral face on one end of this shaft portion 311.

The condyle portion 312 is configured to be in a spherical shape having a diameter greater than that of the shaft portion 311, and is arranged at the central portion of the shaft portion 311 in a longitudinal direction thereof.

In the first embodiment, the shaft portions 311 and the condyle portions 312 are formed from a magnetic material such as iron.

The knob portion 313 is configured from a rigid synthetic resin, and is attached to the other end side of the shaft portion 311 in the longitudinal direction thereof.

The abovementioned projecting portion 31 is coupled with the upper jaw support portion 10 by threading a screw thread formed at one end of the shaft portion 311 into a threaded hole provided in the coupling portion 13.

As shown in FIGS. 1 to 3, the pair of condyle path portions 32 is engaged with the pair of projecting portions 31 (projecting path portions 312 in the first embodiment) so as to rotatably support the lower jaw support portion 20 about the pair of projecting portions 31 (shaft portions 311 in the first embodiment), and slidably support the upper jaw support portion 10 in a first direction D1 (refer to FIGS. 2 and 7).

The pair of condyle path portions 32 is arranged at the rear end of the lower jaw posteriorly extending portions 22. This condyle path portion 32 is configured from a rigid synthetic resin, and is integrally formed with the lower jaw support unit 20.

As shown in FIGS. 4 and 7, the condyle path portion 32 is formed in a substantially U-shape of which a tip end side (rear side) is opened obliquely upward as seen from a lateral side, and is provided with a first retaining portion 321, a first guide portion 322, and a magnet 323.

The first retaining portion 321 is provided at a base end side (front side) of the condyle path portion 32. An inner face of this first retaining portion 321 is configured to include a concave curved face portion corresponding to the shape of the condyle portion 312 (refer to FIG. 4).

The first guide portion 322 is formed continuously to the first retaining portion 321 and extends in a first direction D1. As shown in FIG. 7, in the first embodiment, the first guide portion 322 extends posteriorly and obliquely upward in a state with the lower jaw model 50 fixed to the lower jaw fixing portion 21 being positioned horizontally. The width of this first guide portion 322 is configured to be smaller than a diameter R1 of the condyle portion 312 at the tip end portion (rear end portion) (refer to the width W1 shown in FIGS. 2 and 7), and, at portions other than this tip end portion, is configured to be substantially equal to the diameter of the condyle portion 312 (refer to the width W2 shown in FIGS. 2 and 7).

The magnet 323 is arranged at a base end side of the condyle path portion 32. More specifically, the magnet 323 is attached to a lower face side in the proximity of the rear end portion of the lower jaw posteriorly extending portion 22, and is arranged so that a tip end side of this magnet 323 is exposed to the inner face of the first retaining portion 321 (refer to FIG. 4). It should be noted that the magnet may be either a permanent magnet or an electromagnet. In the case of being a permanent magnet, a neodymium magnet is preferred from the point of an attractive force tending to be sufficiently obtained by the magnetic force thereof.

The abovementioned articulator 1 is assembled in the following sequence.

First, the upper jaw model 40 is fixed to the upper jaw support portion 10 and the lower jaw model 50 is fixed to the lower jaw support portion 20. Then, the pair of projecting portions 31 is made to be engaged with the pair of condyle path portions 32, respectively. More specifically, the pair of projecting portions 31 is engaged therewith by inserting the condyle portion 312 from the open tip end side of the first guide portion 322.

Here, according to the articulator 1 of the first embodiment, the magnet 323 is arranged in the proximity of the first retaining portion 321; therefore, the condyle portion 312 configured by a magnetic material contacts or approaches the magnet 323 by the magnetic force of this magnet 323 so as to be attracted and retained at the first retaining portion 321. The lower jaw support portion 20 can be rotatably supported about the shaft portion 311 in the first retaining portion 321 (refer to FIGS. 2 and 9). Furthermore, since the first guide portion 322 is arranged at the first retaining portion 321 to extend continuously in the first direction D1, the lower jaw support portion 20 is allowed to slide in the first direction D1 with respect to the upper jaw support portion 10 (refer to FIGS. 9 and 10).

The following effects are exerted by the articulator 1 according to the first embodiment as described above.

(1) The joint portion 30 is configured to include the projecting portion 31 and the condyle path portion 32 that engages with this projecting portion 31. Then, the projecting portion 31 is configured to include a magnetic material, and the condyle path portion 32 is configured to include the magnet 323. In this way, by causing the projecting portion 31 to attract by way of magnetic force to a predetermined position on the condyle path portion 32, it is possible to retain the projecting portion 31 at the attracting position of the projecting portion 31 and the condyle path portion 32. Consequently, it becomes possible to configure a coupling mechanism of the joint portion 30 between the upper jaw support portion 10 and the lower jaw support portion 20 in a simple structure.

(2) The condyle path portion 32 is configured to include the first retaining portion 321 and the first guide portion 322 so that the lower jaw support unit 20 is made slidable in the first direction D with respect to the upper jaw support unit 10. In this way, in the case of the projecting portion 31 being made to slide from the first retaining portion 321 that is the attracting position of the condyle path portion 32, the attractive force between the projecting portion 31 and the condyle path portion 32 is greatly reduced; therefore, it is possible to reduce the influence of the attractive force in the case of the projecting portion 31 being made to slide from the first retaining portion 321. Therefore, since the projecting portion 31 can be retained strongly at the first retaining portion 321 of the condyle path portion 32 and the influence of the attractive force can be reduced in the case of the projecting portion 31 sliding from the first retaining portion 321, it is possible to improve the degrees of freedom of the engaging state of the joint portion 30 between the upper jaw support portion 10 and the lower jaw support portion 20.

(3) The projecting portion 31 is configured to include the shaft portion 311 and the condyle portion 312, and the condyle path portion 32 is made to engage with the condyle portion 312. In this way, since it becomes possible to make the configuration of the joint unit 30 similar to the coupling mechanism of the upper jaw and the lower jaw of the human body, it is possible to replicate the jaw movements of the human body more precisely. Furthermore, since the condyle portion 312 is configured in a spherical shape, it is possible to improve the degrees of freedom of adjustment when aligning the positions of the upper jaw support unit 10 and the lower jaw support unit 20.

(4) The one end portion of the first guide portion 322 is set to be open and the width W1 of the first guide portion 322 at this one end portion is configured to be smaller than the diameter of the condyle portion 312. In this way, by inserting the projecting portion 31 (condyle portion 312) from the open tip end side (rear side) of the first guide portion 322, it becomes possible to easily couple the upper jaw support portion 10 with the lower jaw support portion 20, as well as preventing the projecting portion 31 thus inserted from falling from the condyle path portion 32. Therefore, it is possible to improve the degrees of freedom of attachment and detachment of the upper jaw support portion 10 and the lower jaw support portion 20.

Figure 11:
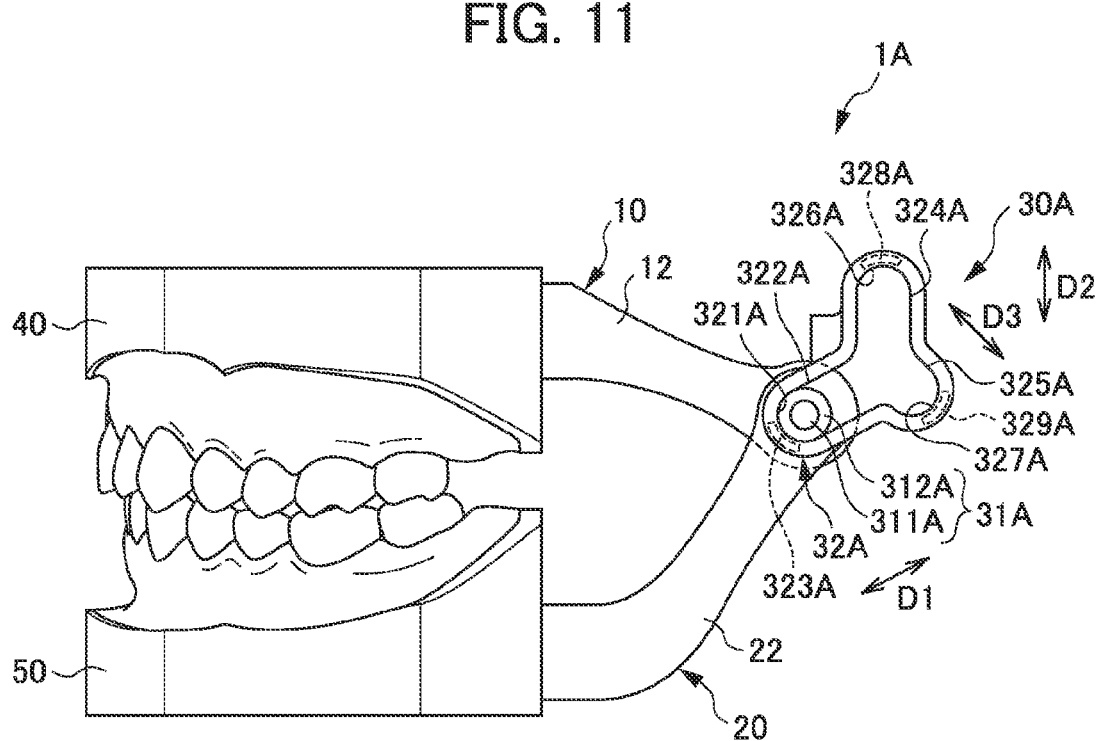
FIG. 11 is a lateral view of the articulator according to a second embodiment and shows a state in which a projecting portion is positioned at a first guide portion.
Figure 12:
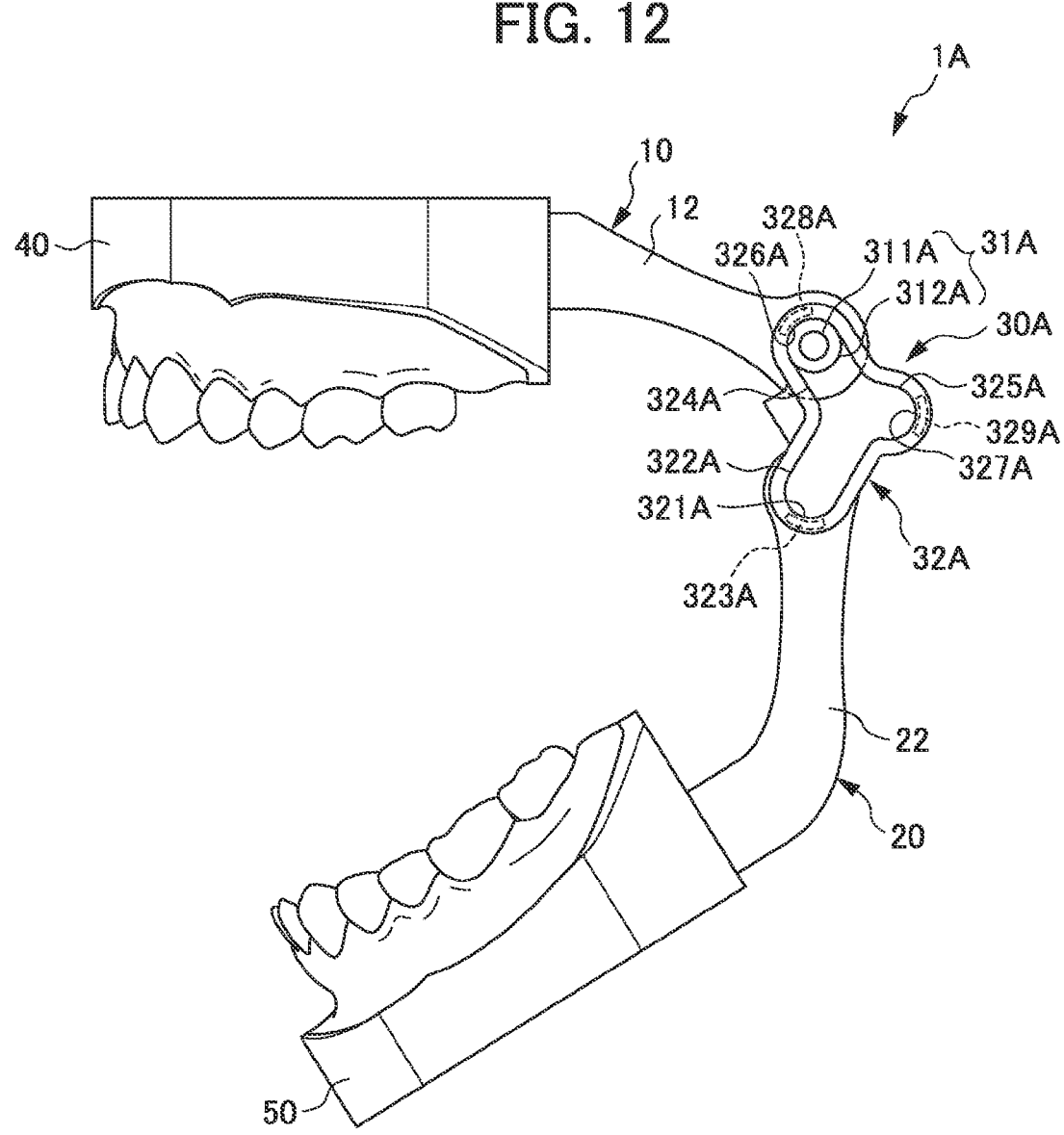
FIG. 12 is a lateral view of an articulator according to the second embodiment and shows a state in which the projecting portion is positioned at a second guide portion.
Figure 13:
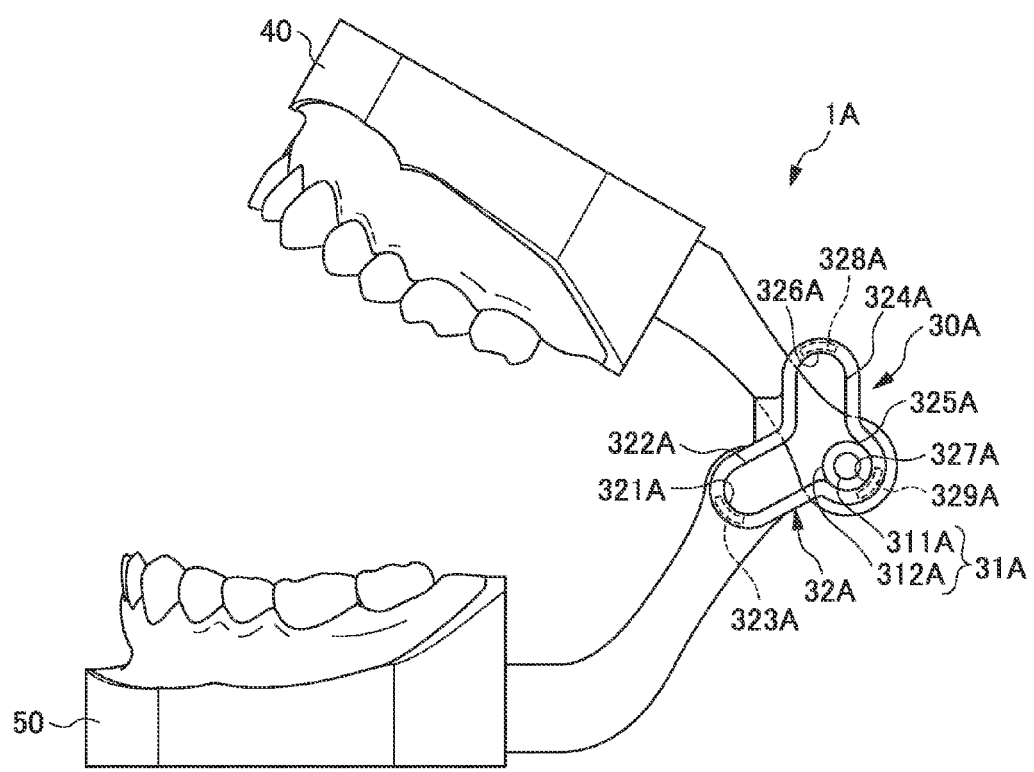
FIG. 13 is a lateral view of the articulator according to the second embodiment and shows a state in which the projecting portion is positioned at a third guide portion.

Next, a second embodiment of an articulator according to the present invention will be explained with reference to FIGS. 11 to 13. FIGS. 11 to 13 are lateral views showing an articulator 1A according to the second embodiment. FIG. 11 is a diagram showing a state in which the projecting portion 31 is positioned at a first retaining portion 321A. FIG. 12 is a diagram showing a state in which the projecting portion 31 is positioned at a second retaining portion 326A, and FIG. 13 is a diagram showing a state in which the projecting portion 31 is positioned at a third retaining portion 327A. It should be noted that, in the explanations of the second and later embodiments, the same reference numerals will be given to similar same constituent elements, and explanations thereof will be omitted or abbreviated.

The articulator 1A according to the second embodiment differs from that of the first embodiment mainly in the configuration of the condyle portion 32A. More specifically, in addition to the first retaining portion 321A, a first guide portion 322A, and a magnet 323A, the condyle path portion 32A of the articulator 1A according to the second embodiment is provided with: a second guide portion 324A and a third guide portion 325A that are continuous with the first guide portion 322A; a second retaining portion 326A that is positioned at a tip end side of the second guide portion 324A; a third retaining portion 327A that is positioned at a tip end side of the third guide portion 325A; a magnet 328A that is positioned at the second retaining portion 326A; and a magnet 329A that is arranged at the third retaining portion 327A.

As shown in FIGS. 11 to 13, the second guide portion 324A is formed to extend in a second direction D2, which intersects with the first direction D1. As shown in FIG. 11, in the second embodiment, the second guide portion 324A extends vertically upward from the tip end portion of the first guide portion 322A in a state with the lower jaw model 50 fixed to the lower jaw fixing portion 21 being positioned horizontally.

The second retaining portion 326A is configured such that a tip end portion of the second guide portion 324A is closed, and the magnet 328A is disposed at the closed tip end portion of the second guide portion 324A.

As shown in FIGS. 11 to 13, the third guide portion 325A is formed to extend in a third direction D3, which intersects with the first direction D1 and the second direction D2. As shown in FIG. 11, in the second embodiment, the third guide portion 325A extends obliquely downward from the tip end portion of the first guide portion 322A in a state with the lower jaw model 50 fixed to the lower jaw fixing portion 21 being positioned horizontally.

The third retaining portion 327A is configured such that a tip end portion of the third guide portion 325A is closed, and the magnet 329A is disposed at the closed tip end portion of the third guide portion 325A.

In addition to the effects of the abovementioned (1) to (3), the following effects are exerted by the articulator 1A according to the second embodiment.

(5) The condyle path portion 32A is configured to include the first guide portion 322A, the second guide portion 324A, and the third guide portion 325A. In this way, sliding is allowed not only in the first direction D1, but also in the second direction D2 and the third direction D3. Therefore, it is possible to improve degrees of freedom of the engaging state of the joint portion 30A between the upper jaw support portion 10 and the lower jaw support portion 20.

(6) The second retaining portion 326A is provided at the tip end side of the second guide portion 324A and the third retaining portion 327A is provided at the tip end side of the third guide portion 325A. The projecting portion 31 can thereby be retained by being attracted by the magnetic force also at the second retaining portion 326A and the third retaining portion 327A; therefore, the projecting portion 31 can be retained at multiple positions for the condyle path portion 32A. Consequently, it is possible to easily replicate the open-close movement between the upper jaw support portion 10 and the lower jaw support portion 20 with the multiple positions of the condyle path portion 32A being set as a rotational axis.

Figure 14A:
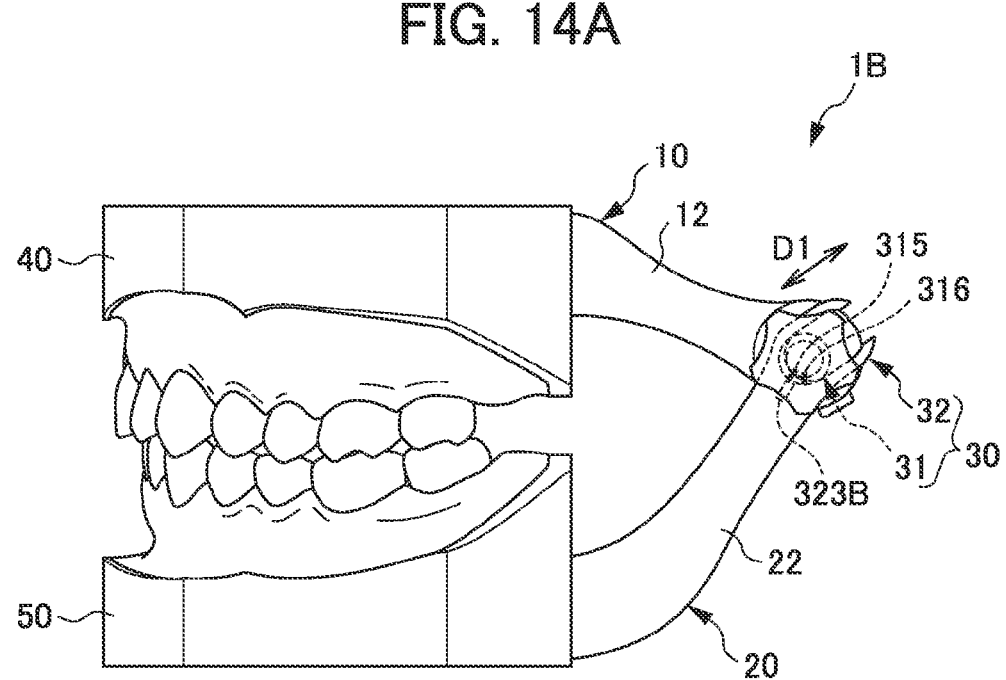
FIG. 14A is a lateral view of an articulator according to a third embodiment and shows a state in which an upper jaw support portion and a lower jaw support portion are closed (closed state)
Figure 14B:
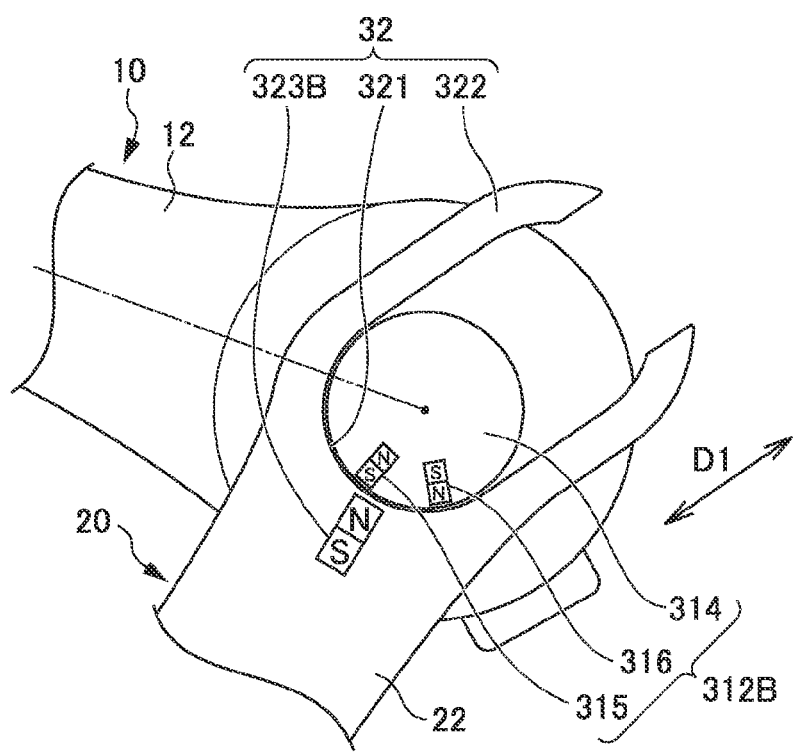
FIG. 14B is a partially enlarged view of FIG. 14A.
Figure 15A:
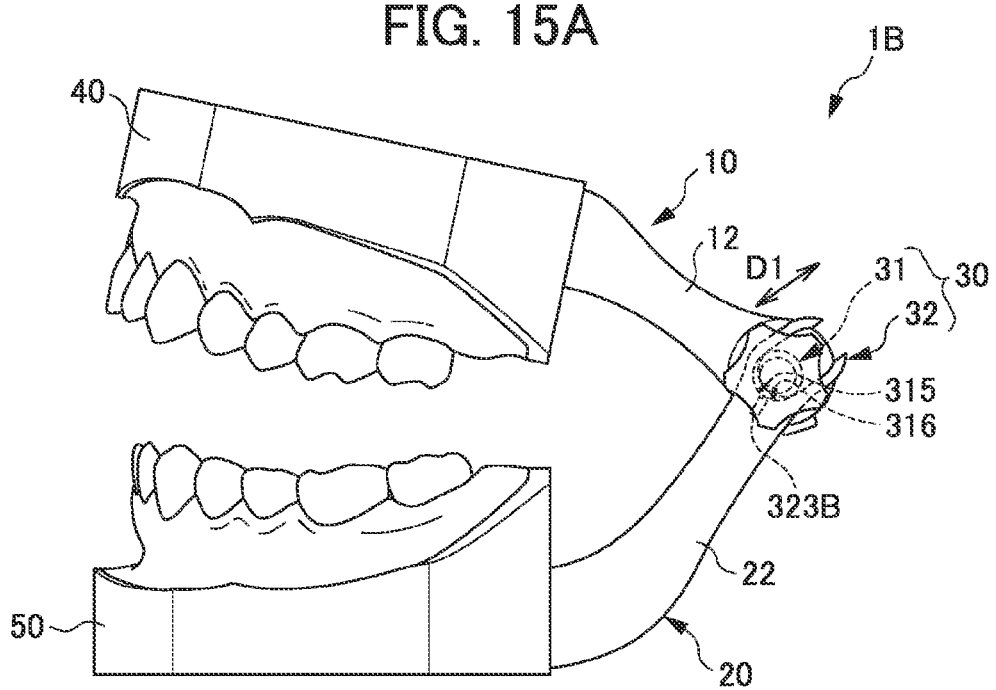
FIG. 15A is a lateral view of the articulator according to the third embodiment and shows a state in which the upper jaw support portion and the lower jaw support portion are opened at a predetermined angle from the closed state.
Figure 15B:
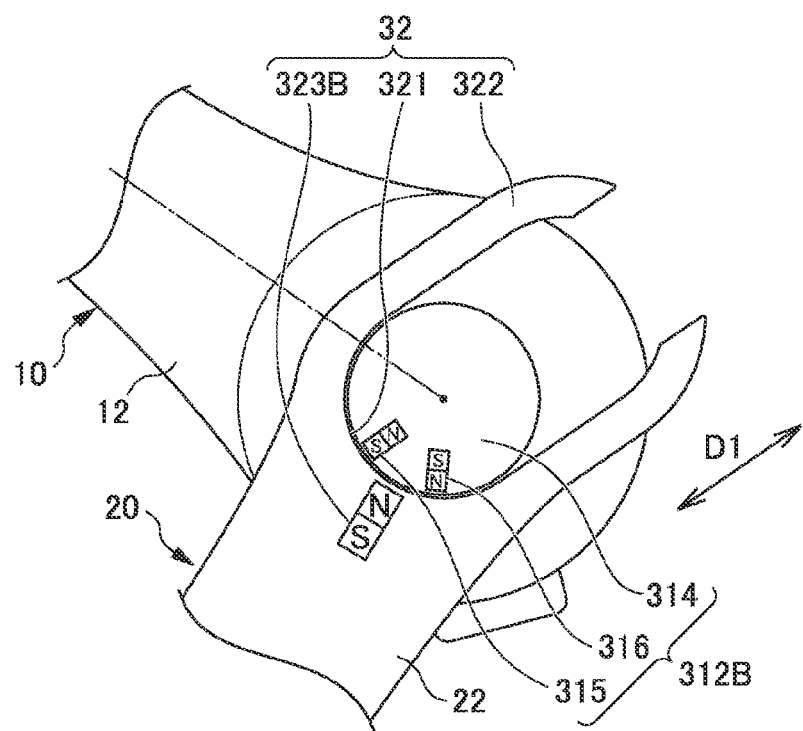
FIG. 15B is a partially enlarged view.
Figure 16A:
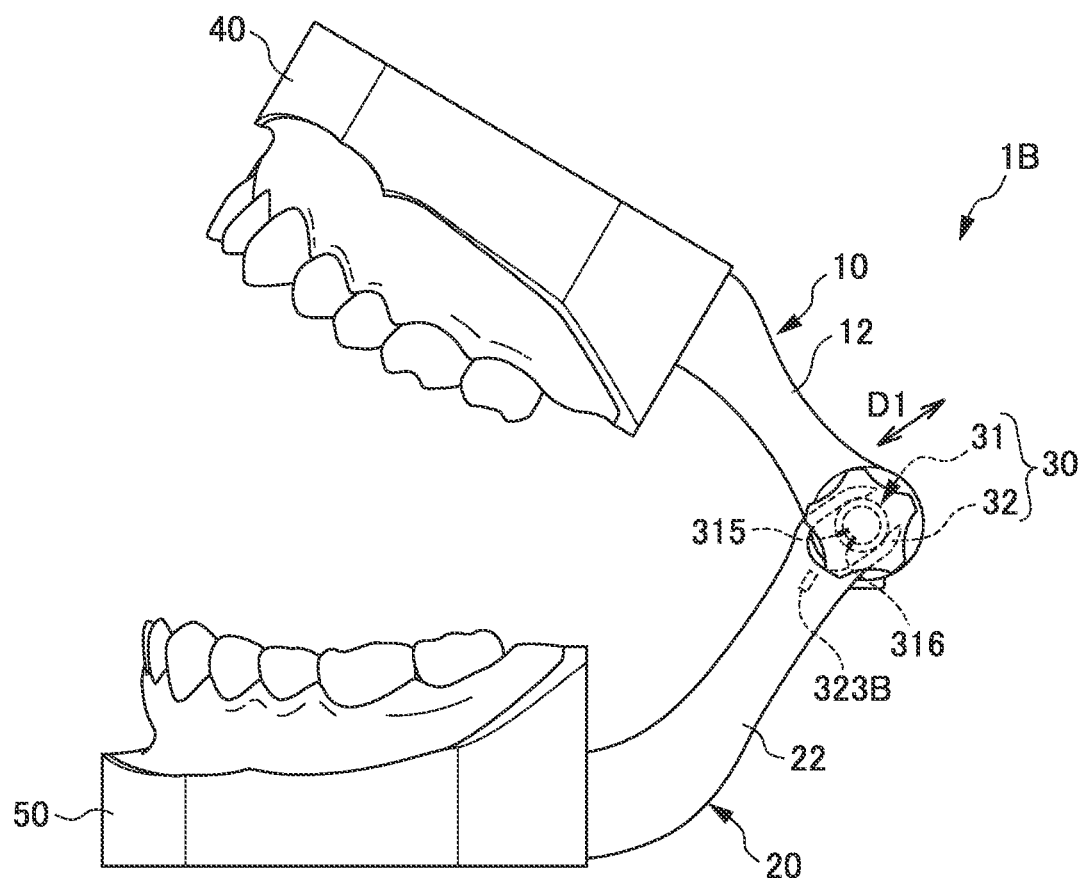
FIG. 16A is a lateral view of the articulator according to the third embodiment and shows a state in which the upper jaw support unit and the lower jaw support unit are further opened from the state shown in FIG. 15A.
Figure 16B:
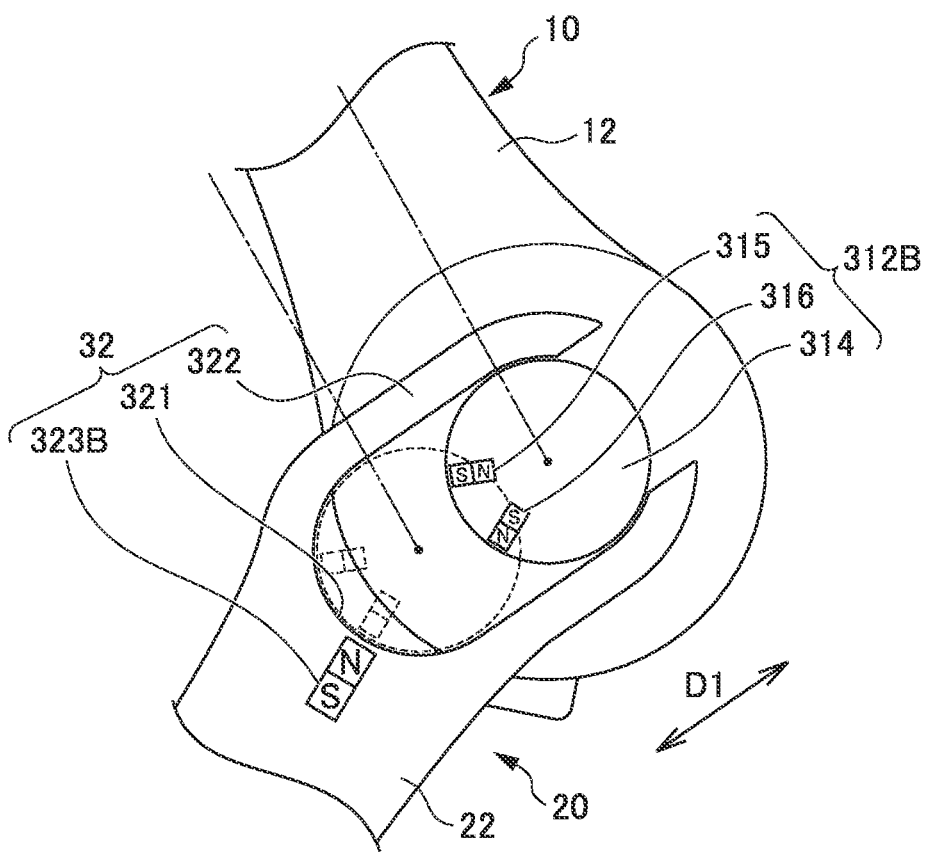
FIG. 16B is a partially enlarged view of FIG. 16A.

Next, a third embodiment of an articulator according to the present invention will be explained with reference to FIGS. 14 to 16. FIGS. 14 to 16 are lateral views showing an articulator 1B according to the third embodiment. FIG. 14A is a diagram showing a state in which the upper jaw support unit 10 and the lower jaw support unit 20 are closed (closed state). FIG. 14B is a partially enlarged view of FIG. 14A. Furthermore, FIG. 15A is a diagram showing a state in which the upper jaw support unit 10 and the lower jaw support unit 20 are opened state by a predetermined angle from the closed state. FIG. 15B is a partially enlarged view of FIG. 15A. FIG. 16A is a diagram showing a state in which the upper jaw support portion 10 and the lower jaw support portion 20 are further opened from the state shown in FIG. 15A. FIG. 16B is a partially enlarged view of FIG. 16A.

The articulator 1B according to the third embodiment is different from the articulator 1 according to the first embodiment in that the attractive force between the projecting portion 31 and the condyle path portion 32 differs between the closed state and the opened state of the articulator 1B. More specifically, the attractive force between the projecting portion 31 and the condyle path portion 32 in the closed state is configured so as to be greater than the attractive force between the projecting portion 31 and the condyle path portion 32 in the opened state.

As shown in FIGS. 14A and 14B, in the third embodiment, a retaining portion side magnet 323B, which is a magnet similar to that in first embodiment, is arranged at the first retaining portion 321. This retaining portion side magnet 323B is arranged such that either the N pole or S pole thereof (for example, N pole) is disposed to be exposed to the inner face of the first retaining portion 321.

Furthermore, the condyle portion 312B is provided with a spherical main body 314, an attraction member 315 embedded in this main body 314, and a projecting portion side magnet 316.

The main body 314 is configured from a nonmagnetic member such of synthetic resin or the like. A concave portion (not illustrated) in which the attraction member 315 and the projecting portion side magnet 316 are embedded is formed at this main body 314.

The attraction member 315 is configured from a member that can be attracted to the retaining portion side magnet 323B. In the third embodiment, the attraction member 315 is configured from a magnet.

As shown in FIGS. 14A and 14B, the attraction member 315 is arranged at a position where the attraction member 315 faces the retaining portion side magnetic 323B that is arranged at the first retaining portion 321 of the condyle portion 312B, in the closed state of the articulator 1B. This attraction member 315 (magnet) is embedded in the concave portion formed in the main body 314 so that a pole different from the pole of the retaining portion side magnet 323B exposed to the inner face of the first retaining portion 321 (for example, S pole) is positioned on the surface of the main body 314. It should be noted that a magnetic member may be used in place of a magnet, for the attraction member 315.

As shown in FIGS. 16A and 16B, the projecting portion side magnet 316 is arranged at a position where the projecting portion side magnet 316 faces the retaining portion side magnet 323B that is arranged at the first retaining portion 321 of the condyle portion 312B, in the opened state in which the articulator 1B is opened by a predetermined angle from the closed state. This projecting member 316 is embedded in the concave portion formed in the main body 314 so that a pole identical to the pole of the retaining portion side magnet 323B exposed to the inner face of the first retaining portion 321 (for example, N pole) is positioned on the surface of the main body 314.

The articulator 1B according to the third embodiment operates as follows.

First, as shown in FIGS. 14A and 14B, the attraction member 315 and the retaining portion side magnet 323B are arranged at positions facing each other in the closed state of the articulator 1B. Therefore, when the articulator 1B is in the closed state, the upper jaw support unit 10 and the lower jaw support unit 20 are coupled with the condyle portion 312B being attracted to the inner face of the first retaining portion 321.

Next, as shown in FIGS. 15A and 15B, when the articulator 1B is opened from the state shown in FIG. 14, the main body 314 of the condyle portion 312B is arranged at a position facing the retaining portion side magnet 323B. In this state, since the attractive force from the magnet does not occur between the condyle portion 312B and the first retaining portion 321, the degrees of freedom of the relative movement in the first direction D1 between the upper jaw support portion 10 and the lower jaw support portion 20 is improved.

Then, as shown in FIGS. 16A and 16B, when the articulator 1B is opened further from the state shown in FIG. 15, the projecting portion side magnet 316 at the condyle portion 312B and the retaining portion side magnet 323B are arranged at positions facing each other. Here, since the projecting portion side magnet 316 and the retaining portion side magnet 323B both expose the surfaces of identical pole, a repelling force occurs between the condyle portion 312B and the first retaining portion 321. In this way, the upper jaw support portion 10 and the lower jaw support portion 20 are coupled in a state with the condyle portion 312B being spaced apart from the inner face of the first retaining portion 321.

In addition to the effects of the abovementioned (1) to (4), the following effects are exerted by the articulator 1B according to the third embodiment.

(7) The attractive force between the condyle portion 312 and the first retaining portion 321 in the closed state is configured to be greater than the attractive force between the condyle portion 312B and the first retaining portion 321 in the opened state. In this way, it is possible to reduce the attractive force between the condyle portion 312B and the first retaining portion 321 when the articulator 1B is set to be in the opened state. Therefore, it is possible to improve degrees of freedom of the engaging state between the upper jaw support portion 10 and the lower jaw support portion 20 when the articulator 1B is in the opened state.

(8) The condyle path portion 32 is configured to include the retaining portion side magnet 323B that is arranged at the first retaining portion 321, and the condyle portion 312B is configured to include: the attraction member 315 that is arranged at a position facing the first retaining portion 321 when the articulator 1B is in the closed state; and the projecting portion side magnet 316 that is arranged at a position facing the first retaining portion 321 when the articulator 1B is in the opened state so as to repel the retaining portion side magnet 323B. In this way, when the articulator 1B is in the opened state, the upper jaw support portion 10 and the lower jaw support portion 20 are coupled in a state with the condyle portion 312B and the first retaining portion 321 being spaced apart from each other in the first direction D1. Therefore, in the opened state, it becomes possible to easily replicate an articulating state, which is different from the closed state.

Although each of the preferred embodiments of an articulator according to the present invention has been explained in the foregoing, the present invention is not limited to the abovementioned embodiments and can be implemented in various forms.

For example, although the condyle portion 312 is configured from a magnetic material and a magnet is arranged at the condyle portion 32 in the first to third embodiments, the present invention is not limited thereto. In other words, the condyle portion may be configured from a magnet and the magnetic material may be arranged at the condyle portion. In addition, the condyle portion and the condyle path portion may be configured from an electromagnet.

Furthermore, although the projecting portion 31 is provided at the upper jaw support portion 10 and the condyle path portion 32 is provided at the lower jaw support portion 20 in the first to third embodiments, the present invention is not limited thereto. In other words, the condyle path portion may be provided at the upper jaw support portion and the projecting portion may be provided at the lower jaw support portion.

Furthermore, although the condyle portion 312 is configured in a spherical shape in the first and third embodiments, the present invention is not limited thereto. In other words, the condyle portion may be configured in a cylindrical shape having a diameter greater than the diameter of the shaft portion.

Moreover, although the width of the open tip end side of the first guide portion 322 is set to be smaller than the diameter of the condyle portion 312 in the first embodiment to the third embodiment, the present invention is not limited thereto. In other words, the tip end side of the first guide portion may be configured to be equal to the diameter of the condyle portion, or may be configured to be greater than the diameter of the condyle portion.

Furthermore, although the condyle path portion 32 is configured to include the first retaining portion 321 and the first guide portion 322 in the first and third embodiments, the present invention is not limited thereto. In other words, the condyle path portion may be configured by the retaining portion solely.

Furthermore, although the condyle path portion 32A is configured to include the first guide portion 322A, the second guide portion 324A, and the third guide portion 325A, and the projecting portion 31 is configured to be slidable in the three directions of the first direction D1, the second direction D2, and the third direction D3 in the second embodiment, the present invention is not limited thereto. In other words, the sliding direction of the projecting portion may be in two directions or may be four or more directions.

The present invention can be preferably used as an articulator for demonstration used for teaching practice or coaching, and as an articulator for dental technicians used when fabricating an artificial tooth and dental prosthesis.

What is claimed is:

1. An articulator comprising:
    a first support unit to which a first dental model is fixed at a front side of the first support unit and that supports the first dental model;

a second support unit to which a second dental model is fixed at a front side of the second support unit and that supports the second dental model; and a joint portion that couples a rear side of the first support unit and a rear side of the second support unit, wherein the joint portion includes:

a pair of projecting portions having a shaft portion that is provided at the rear side of the first support unit and projects in left and right directions, respectively; and an engaging support portion that is provided at the rear side of the second support unit to engage with the pair of projecting portions so as to rotatably support the second support unit about the pair of projecting portions, wherein the projecting portion and the engaging support portion are attractable to each other by way of magnetic force, wherein the engaging support portion is formed integrally with the second support unit, and wherein the engaging support portion comprises:

a first retaining portion that is arranged at a base end side of the engaging support portion and has a concave curved face portion configured to guide the projecting portion, a magnet that is arranged on an inner face of the concave curved face portion of the first retaining portion, so as to attract the projecting portion by way of a magnetic force to a predetermined position of the engaging support portion, and a first guide portion that is formed continuously to the first retaining portion, arranged on the opposite side of the base end side of the engaging support portion and extends in a first direction orthogonal to the shaft portion, wherein the second support unit is coupled to the first support unit and configured to be slidable in the first direction along the first guide portion with respect to the first support unit, wherein the projecting portion includes a spherical condyle portion provided at the shaft portion, wherein the condyle portion engages with the first retaining portion by way of magnetic force and connects to the first guide portion away from the first retaining portion, and wherein a tip end side of the first guide portion is opened and a width of the first guide portion at the tip end side thereof is smaller than a diameter of the condyle portion, and wherein transfer of the condyle portion into and from the first guide portion is via the opening at the tip end side of the first guide portion, and the condyle portion and the first retaining portion are engaged via the first guide portion.

2. The articulator according to claim 1, wherein the condyle portion includes either one of a magnet or a magnetic material.

3. The articulator according to claim 2, wherein, in a state in which the condyle portion is engaged with the first retaining portion, an attractive force between the projecting portion and the first retaining portion in a closed state in which the first support unit and the second support unit are closed is greater than an attractive force between the projecting portion and the first retaining portion in an opened state in which the first support unit and the second support unit are opened.

4. The articulator according to claim 3, further comprising:

an attraction member that is arranged at a position on the projecting portion facing the first retaining portion and that can be attracted to the retaining portion side magnet in the closed state; and a projecting portion side magnet that is arranged at a position on the projecting portion facing the first retaining portion and that repels the retaining portion side magnet in the opened state.

5. The articulator according to claim 3, wherein the engaging support portion includes:

a second guide portion that is provided continuously to the first guide portion at the tip end side of the first guide portion and extends in a second direction;

a second retaining portion that is provided to a base end side of the second guide portion, opposite to a tip end side of the first guide portion, the second retaining portion having a concave curved face portion for guiding the projecting portion;

a magnet that is arranged on an inner face of the concave curved face portion of the second retaining portion, so as to attract the projecting portion by way of a magnetic force to a predetermined position of the engaging support portion;

a third guide portion that is provided continuously to the first guide portion and the second guide portion at the tip end side of the first guide portion and extends in a third direction;

a third retaining portion that is provided to a base end side of the third guide portion, opposite to the tip end side of the first guide portion, the third retaining portion having a concave curved face portion for guiding the projecting portion; and a magnet that is arranged on an inner face of the concave curved face portion of the third retaining portion, so as to attract the projecting portion by way of a magnetic force to a predetermined position of the engaging support portion.

6. The articulator according to claim 1, wherein a tip end side of the magnet is exposed to the inner face of the concave curved face portion of the first retaining portion.

7. The articulator according to claim 1, wherein the engaging support portion further includes:

a second guide portion that is provided continuously to the first guide portion at the tip end side of the first guide portion and extends in a second direction;

a second retaining portion that is provided to a base end side of the second guide portion, opposite to a tip end side of the first guide portion, the second retaining portion having a concave curved face portion for guiding the projecting portion;

a magnet that is arranged on an inner face of the concave curved face portion of the second retaining portion, so as to attract the projecting portion by way of a magnetic force to a predetermined position of the engaging support portion;

a third guide portion that is provided continuously to the first guide portion and the second guide portion at the tip end side of the first guide portion and extends in a third direction;

a third retaining portion that is provided to a base end side of the third guide portion, opposite to the tip end side of the first guide portion, the third retaining portion having a concave curved face portion for guiding the projecting portion; and a magnet that is arranged on an inner face of the concave curved face portion of the third retaining portion, so as to attract the projecting portion by way of a magnetic force to a predetermined position of the engaging support portion.

8. The articulator according to claim 1, wherein the magnet is embedded in the inner face of the concave curved face portion of the first retaining portion.

9. The articulator according to claim 8, wherein the engaging support portion includes:
   a second guide portion that is provided continuously to the first guide portion at the tip end side of the first guide portion and extends in a second direction;
   a second retaining portion that is provided to a base end side of the second guide portion, opposite to a tip end side of the first guide portion, the second retaining portion having a concave curved face portion for guiding the projecting portion;
   a magnet that is arranged on an inner face of the concave curved face portion of the second retaining portion, so as to attract the projecting portion by way of a magnetic force to a predetermined position of the engaging support portion;
   a third guide portion that is provided continuously to the first guide portion and the second guide portion at the tip end side of the first guide portion and extends in a third direction;
   a third retaining portion that is provided to a base end side of the third guide portion, opposite to the tip end side of the first guide portion, the third retaining portion having a concave curved face portion for guiding the projecting portion; and
   a magnet that is arranged on an inner face of the concave curved face portion of the third retaining portion, so as to attract the projecting portion by way of a magnetic force to a predetermined position of the engaging support portion.

10. An articulator comprising:
    a first support unit to which a first dental model is fixed at a front side of the first support unit and that supports the first dental model;
    a second support unit to which a second dental model is fixed at a front side of the second support unit and that supports the second dental model; and
    a joint portion that couples a rear side of the first support unit and a rear side of the second support unit, wherein the joint portion includes:
    a pair of projecting portions having a shaft portion that is provided at the rear side of the first support unit and projects in left and right directions, respectively; and
    an engaging support portion that is provided at the rear side of the second support unit to engage with the pair of projecting portions so as to rotatably support the second support unit about the pair of projecting portions,
    wherein the projecting portion and the engaging support portion are attractable to each other by way of magnetic force,
    wherein the engaging support portion is formed integrally with the second support unit, and
    wherein the engaging support portion comprises:
    a first retaining portion that is arranged at a base end side of the engaging support portion and has a concave curved face portion configured to guide the projecting portion,
    a magnet that is arranged on an inner face of the concave curved face portion of the first retaining portion, so as to attract the projecting portion by way of a magnetic force to a predetermined position of the engaging support portion, and
    a first guide portion that is formed continuously to the first retaining portion, arranged on the opposite side of the base end side of the engaging support portion and extends in a first direction orthogonal to the shaft portion,
    wherein the second support unit is coupled to the first support unit to be slidable in the first direction with respect to the first support unit,
    wherein the projecting portion includes a spherical condyle portion provided at this shaft portion, wherein the condyle portion engages with the first retaining portion by way of magnetic force and connections to the first guide portion away from the first retaining portion, and
    wherein a tip end side of the first guide portion is opened, and wherein transfer of the condyle portion into and from the first guide portion is via the opening at the tip end side of the first guide portion, and the condyle portion and the first retaining portion are engaged via the first guide portion.

11. The articulator according to claim 10, wherein the condyle portion includes either one of a magnet or a magnetic material.

12. The articulator according to claim 10, wherein, in a state in which the condyle portion is engaged with the first retaining portion, an attractive force between the projecting portion and the first retaining portion in a closed state in which the first support unit and the second support unit are closed is greater than an attractive force between the projecting portion and the first retaining portion in an opened state in which the first support unit and the second support unit are opened.

13. The articulator according to claim 12, further comprising:
    an attraction member that is arranged at a position on the projecting portion facing the first retaining portion and that can be attracted to the retaining portion side magnet in the closed state; and
    a projecting portion side magnet that is arranged at a position on the projecting portion facing the first retaining portion and that repels the retaining portion side magnet in the opened state.

14. The articulator according to claim 10, wherein the engaging support portion further includes:
    a second guide portion that is provided continuously to the first guide portion at the tip end side of the first guide portion and extends in a second direction;
    a second retaining portion that is provided to a base end side of the second guide portion, opposite to a tip end side of the first guide portion, the second retaining portion having a concave curved face portion for guiding the projecting portion;
    a magnet that is arranged on an inner face of the concave curved face portion of the second retaining portion, so as to attract the projecting portion by way of a magnetic force to a predetermined position of the engaging support portion;
    a third guide portion that is provided continuously to the first guide portion and the second guide portion at the tip end side of the first guide portion and extends in a third direction;
    a third retaining portion that is provided to a base end side of the third guide portion, opposite to the tip end side of the first guide portion, the third retaining portion having a concave curved face portion for guiding the projecting portion; and
    a magnet that is arranged on an inner face of the concave curved face portion of the third retaining portion, so as to attract the projecting portion by way of a magnetic force to a predetermined position of the engaging support portion.

15. An articulator comprising:
a first support unit to which a first dental model is fixed at a front side of the first support unit and that supports the first dental model;
a second support unit to which a second dental model is fixed at a front side of the second support unit and that supports the second dental model; and
a joint portion that couples a rear side of the first support unit and a rear side of the second support unit, wherein the joint portion includes:
  a pair of projecting portions having a shaft portion that is provided at the rear side of the first support unit and projects in left and right directions, respectively; and
  an engaging support portion that is provided at the rear side of the second support unit to engage with the pair of projecting portions so as to rotatably support the second support unit about the pair of projecting portions,
  wherein the projecting portion and the engaging support portion are attractable to each other by way of magnetic force,
  wherein the engaging support portion is formed integrally with the second support unit, and
  wherein the engaging support portion comprises:
  a first retaining portion that is arranged at a base end side of the engaging support portion and has a concave curved face portion configured to guide the projecting portion,
  a magnet that is arranged on an inner face of the concave curved face portion of the first retaining portion, so as to attract the projecting portion by way of a magnetic force to a predetermined position of the engaging support portion, and
  a first guide portion that is formed continuously to the first retaining portion, arranged on the opposite side of the base end side of the engaging support portion and extends in a first direction orthogonal to the shaft portion,
  wherein the second support unit is coupled to the first support unit to be slidable in the first direction with respect to the first support unit,
  wherein the projecting portion includes a spherical condyle portion provided at this shaft portion, wherein the condyle portion engages with the first retaining portion by way of magnetic force and connections to the first guide portion away from the first retaining portion, and
  wherein, at an end side of the first guide portion opposite to the base end side of the engaging support portion, the condyle portion can become free from sliding motion in the first direction that the first guide portion is guiding.

16. The articulator according to claim 15, wherein the condyle portion includes either one of a magnet or a magnetic material.

17. The articulator according to claim 15, wherein, in a state in which the condyle portion is engaged with the first retaining portion, an attractive force between the projecting portion and the first retaining portion in a closed state in which the first support unit and the second support unit are closed is greater than an attractive force between the projecting portion and the first retaining portion in an opened state in which the first support unit and the second support unit are opened.

18. The articulator according to claim 17, further comprising:
  an attraction member that is arranged at a position on the projecting portion facing the first retaining portion and that can be attracted to the retaining portion side magnet in the closed state; and
  a projecting portion side magnet that is arranged at a position on the projecting portion facing the first retaining portion and that repels the retaining portion side magnet in the opened state.

19. The articulator according to claim 15, wherein the engaging support portion includes:
  a second guide portion that is provided continuously to the first guide portion at the tip end side of the first guide portion and extends in a second direction;
  a second retaining portion that is provided to a base end side of the second guide portion, opposite to a tip end side of the first guide portion, the second retaining portion having a concave curved face portion for guiding the projecting portion;
  a magnet that is arranged on an inner face of the concave curved face portion of the second retaining portion, so as to attract the projecting portion by way of a magnetic force to a predetermined position of the engaging support portion;
  a third guide portion that is provided continuously to the first guide portion and the second guide portion at the tip end side of the first guide portion and extends in a third direction;
  a third retaining portion that is provided to a base end side of the third guide portion, opposite to the tip end side of the first guide portion, the third retaining portion having a concave curved face portion for guiding the projecting portion; and
  a magnet that is arranged on an inner face of the concave curved face portion of the third retaining portion, so as to attract the projecting portion by way of a magnetic force to a predetermined position of the engaging support portion.

* * * * *